(12) United States Patent
Norrby

(10) Patent No.: US 8,206,365 B2
(45) Date of Patent: Jun. 26, 2012

(54) PANT-TYPE ABSORBENT ARTICLE AND A METHOD FOR ITS MANUFACTURE

(75) Inventor: Niclas Norrby, Göteborg (SE)

(73) Assignee: SCA Hygiene Products AB, Göteborg (SE)

( * ) Notice: Subject to any disclaimer, the term of this patent is extended or adjusted under 35 U.S.C. 154(b) by 877 days.

(21) Appl. No.: 11/848,556

(22) Filed: Aug. 31, 2007

(65) Prior Publication Data
US 2008/0009817 A1    Jan. 10, 2008

Related U.S. Application Data

(63) Continuation of application No. PCT/SE2005/000309, filed on Mar. 2, 2005.

(51) Int. Cl.
*A61F 13/15* (2006.01)
*A61F 13/20* (2006.01)

(52) U.S. Cl. .......... 604/385.22; 604/385.24; 604/385.27

(58) Field of Classification Search .......... 604/393–395, 604/397, 402, 385.22, 385.24–385.27
See application file for complete search history.

(56) References Cited

U.S. PATENT DOCUMENTS

| | | | |
|---|---|---|---|
| 4,938,753 A * | 7/1990 | Van Gompel et al. | ... 604/385.29 |
| 5,336,545 A * | 8/1994 | Morman | ...... 428/152 |
| 5,779,831 A | 7/1998 | Schmitz | |
| 6,476,289 B1 | 11/2002 | Buell et al. | |
| 6,552,245 B1 | 4/2003 | Roessler et al. | |
| 2003/0036739 A1 | 2/2003 | Christoffel et al. | |
| 2003/0097110 A1* | 5/2003 | Erdman | ...... 604/385.3 |
| 2003/0163104 A1* | 8/2003 | Tears et al. | ...... 604/378 |
| 2004/0243086 A1 | 12/2004 | VanGompel et al. | |
| 2005/0004549 A1 | 1/2005 | Maas et al. | |
| 2005/0010186 A1* | 1/2005 | Otsubo et al. | ...... 604/385.27 |
| 2005/0080394 A1 | 4/2005 | Otsubo et al. | |
| 2005/0126689 A1 | 6/2005 | Thorson et al. | |
| 2008/0234651 A1 | 9/2008 | Otsubo et al. | |

FOREIGN PATENT DOCUMENTS

EP   1 035 818 B1   9/2000

(Continued)

OTHER PUBLICATIONS

English translation of specification of JP 08-089529 A to Tsubata et al.*

(Continued)

*Primary Examiner* — Melanie Hand

(74) *Attorney, Agent, or Firm* — Buchanan Ingersoll & Rooney PC

(57) ABSTRACT

A pant-type absorbent article, at least one of the front and back panels having an elastic web material constituting the sole component of at least part of the front and/or back panels, the elastic waistband being joined to the waist edge of at least one of the front and back panels, wherein the elastic waistband having a first and a second ply of substantially non-elastic web material enclosing between them at least one elongate elastic member, the first ply of substantially non-elastic web material being secured to one side of the elastic web material at the waist edge of at least one of the front and back panels and that the second ply of substantially non-elastic web material is secured to the opposite side of the elastic web material just opposite said first ply.

31 Claims, 5 Drawing Sheets

FOREIGN PATENT DOCUMENTS

| | | |
|---|---|---|
| JP | 3-205053 A | 9/1991 |
| JP | H08-089529 A | 4/1996 |
| JP | H08-196566 A | 8/1996 |
| JP | 10-043235 A | 2/1998 |
| JP | 2003-290284 A | 10/2003 |
| JP | 2004-229978 A | 8/2004 |
| WO | WO 03/047488 A1 | 6/2003 |
| WO | WO 2004/108039 A1 | 12/2004 |
| WO | WO 2004108039 A1 * | 12/2004 |
| WO | WO 2005/122984 A1 | 12/2005 |
| WO | WO 2005/122985 A1 | 12/2005 |
| WO | WO 2006/038837 A1 | 4/2006 |

OTHER PUBLICATIONS

Form PCT/ISA/210 (International Search Report) dated Oct. 4, 2005.

Form PCT/ISA/237 (Written Opinion of the International Searching Authority) dated Oct. 4, 2005.

English translation of a Notice of Reasons for Rejection issued Jun. 1, 2010 in corresponding Japanese Patent Application No. 2007-557956.

Office Action issued on Mar. 15, 2011, in corresponding Japanese Patent Application No. 2007-557956.

\* cited by examiner

PANT-TYPE ABSORBENT ARTICLE AND A METHOD FOR ITS MANUFACTURE

CROSS-REFERENCE TO RELATED APPLICATIONS

The present application is a continuation of PCT International Application No. PCT/SE2005/000309, filed on Mar. 2, 2005, and which designates the U.S. The entire contents of PCT/SE2005/000309 is incorporated herein by reference.

TECHNICAL FIELD

The present invention refers to a pant-type absorbent article such as a pant diaper, a sanitary pant or incontinence garment, said article comprising an elastic web material. The invention further refers to a method for joining a separate elastic waistband to a pant-type absorbent article.

BACKGROUND OF THE INVENTION

Absorbent articles having defined core regions and chassis regions are supposed to have a comfortable fit about the wearer. For pant articles like pant diapers, sanitary pants and incontinence pants it is also desirable that the articles are capable of being pulled up and down over the hips of the wearer to allow the wearer or caregiver to easily put on and remove the article when it has been soiled. It is known to make such absorbent pants with elasticized stretchable side panels and waist portion, usually comprising elastic members, such as elastic threads, contractably affixed between the backsheet and the topsheet.

It is further known to make portions of the chassis of absorbent articles of an elastic material, such as stretch-bonded laminates. Such laminates may include a layer of meltblown elastomeric fibers which have been stretched and sandwiched between outer layers of spunbonded webs.

U.S. Pat. No. 6,552,245 discloses an extensible outer cover for an absorbent article which provides a certain permanent deformation when subjected to a tensile force. The extensible outer cover comprises a necked laminate in the form of one layer of a necked non-elastic film and one layer of an elastic film. The films may be breathable.

WO 03/047488 discloses an elastic laminate comprising an elastic film which on opposite sides is bonded to first and second non-elastic fibrous layers. The laminate is made by bonding the non-elastic fibrous layers to the elastic film layer and subsequently stretching the composite material, causing the non-elastic materials to break. The elastic film material may be of a breathable material. The laminate may be incorporated in an absorbent article.

US 2004/0243086 discloses a disposable pant-like undergarment having stretchable front and back panels, for example made of an elastic laminate. An elastic waist band is secured to the distal edge of at least one of the front and back panels, said elastic waistband having a retracted length which is less than the retracted length of the panel to which is it attached. The elastic waistband comprises a folded non-elastic web member enclosing one or more elongate elastic members. The elastic waistband is made in a separate manufacturing step and is secured to the distal edge of the front and/or back panel in a semi-stretched condition on the side of said panel facing away from the wearer.

Further examples of absorbent articles which in part are made of elastic laminates are found in U.S. Pat. No. 6,476,289 and JP 10043235.

International applications PCT/SE2004/001004, PCT/SE2004/001005 and PCT/SE2004/001415 refer to absorbent articles comprising an outer coversheet in the form of an elastic laminate having improved properties such as cloth-like feel an appearance. An elastic waistband is secured to the waist edge of the outer coversheet.

Japanese patent publication no. 03-205053 discloses a pant diaper having an elastic waistband secured separately to the diaper chassis, the waistband being folded over the distal edges of the diaper chassis. The diaper chassis comprises a conventional liquid permeable topsheet and a liquid impermeable backsheet, which normally are inelastic, and having an absorbent structure enclosed there between.

There is however still need for improvement of the properties of absorbent articles comprising an elastic web material, such as an elastic laminate, as an outer coversheet, particularly their fit and appearance at the waist opening. The comfort and soft feel of absorbent articles of the above mentioned type is also important as well as the cost aspect including manufacturing costs for disposable articles, which are discarded after one single use.

OBJECT AND SUMMARY

An object of the present disclosure is to provide a pant-type absorbent article having a core region and a front and a back panel comprising an elastic web material constituting the sole component of at least part of the front and/or back panels, said article further having an elastic waistband being joined to the elastic web material in such a way so as to provide an excellent fit and appearance around the waist opening. The waistband comprises a first and a second ply of non-elastic web material enclosing between them at least one elongate elastic member, wherein the first ply of non-elastic web material is secured to one side of the elastic web material at the waist edge of at least one of the front and back panels and the second ply of non-elastic web material is secured to the opposite side of the elastic web material just opposite the first ply. The first and second plies are secured to the elastic web material while this is in a stretched condition. The first and second plies of non-elastic web material with the elastic web material held there between form a waistband seam, wherein the first and second plies of non-elastic material form gathers along said waistband seam when said elastic web material is in a relaxed position.

In one embodiment the elastic waistband is formed from a folded non-elastic web material so as to form said first and second plies enclosing said at least one elongate elastic member.

In one aspect of the disclosure the elastic web material constitutes the sole component of the chassis in at least 20% of the total surface area of the article.

According to one embodiment, the elastic web material is a laminate composed of first and second layers of fibrous material and an elastic film layer located between said first and second fibrous layers, In a further embodiment the elastic film layer is breathable.

In one aspect of the disclosure, the elastic laminate has a Water Vapour Transmission Rate according to ASTM E96-00 Procedure D of at least 1500 $g/m^2$ 24 h, preferably at least 3000 $g/m^2$ 24 h.

According to one embodiment said elastic laminate comprises first and second fibrous layers of spunbond material, each having a basis weight of between 10 and 35 $g/m^2$, preferably between 12 and 30 $g/m^2$, more preferably between 10 and 25 $g/m^2$, and a breathable elastic film layer having a basis weight between 20 and 80 $g/m^2$, preferably between 20 and 60 g/m², said elastic laminate having a Water Vapour Transmission Rate according to ASTM E96-00 Procedure D of at least 1500 g/m² 24 h, preferably at least 3000 g/m² 24 h.

According to a further embodiment said elastic web material has an elasticity in the transverse direction of the article of at least 30%, preferably at least 50%, more preferably at least 70%, when measured according to the elasticity test specified in the description.

In one aspect of the disclosure, the elastic web material has a basis weight of no more than 100 g/m², preferably no more than 90 g/m².

In a still further embodiment a substantially inelastic web material is arranged in the crotch portion of the article, said inelastic web material being joined to the front and back panels comprising said elastic web material.

According to one embodiment the surface area of the absorbent core amounts to no more than 30%, preferably not more than 20%, of the total surface area of the article, as measured in a flat state of the article. The term "flat state" herein means in an opened untensioned state, as seen in FIG. 2 of the drawings, and in which any tensioned elastic members have been deactivated.

The disclosure further refers to a method for joining a separate elastic waistband to a pant-type absorbent article wherein the elastic waistband comprises a first and a second ply of substantially non-elastic web material enclosing between them at least one elongate elastic member and said first and second plies of substantially non-elastic web material are joined to an elastic web material constituting the sole component of at least part of the front and/or back panels of the article. The elastic web material and the substantially non-elastic web material are fed substantially in parallel in a feeding direction (A), each of said web materials having a pair of longitudinal side edges, said elastic web material being fed in a selectively stretched condition;

a first longitudinal side edge of the elastic web material is brought to overlap a selected distance with a first longitudinal side edge of the substantially non-elastic web material and the overlapping side edges are joined to each other, wherein the elastic web material is stretched to a length which exceeds its untensioned length with at least 10% while being joined to the substantially non-elastic web material; at least one elongate elastic member is provided and joined it to the substantially non-elastic web material;

the substantially non-elastic web material is folded in a direction generally transverse to said feeding direction (A), over the at least one elongate elastic member, and the second longitudinal edge of the substantially non-elastic web material is joined in an overlapping manner to the first longitudinal edge of the elastic web material to an opposite side thereof with respect to the first longitudinal edge of the substantially non-elastic web material, so that the first side edge of the elastic web material is held between the first and second side edges of the substantially non-elastic web material, wherein the elastic web material is stretched to a length which exceeds its untensioned length with at least 10% while being joined to the substantially non-elastic web material.

Alternatively to folding the substantially non-elastic web material, a further substantially non-elastic web material is provided and joined to it in an overlapping manner to the first longitudinal edge of the elastic web material to an opposite side thereof with respect to the first substantially non-elastic web material, while the elastic web material is held in said stretched condition, and the free side edges of the two substantially non-elastic web materials are joined to each other in a preceding or subsequent step.

The elastic web material and the substantially elastic web materials are joined to each other by thermal bonding, ultrasonic welding or by adhesive, preferably by ultrasonic welding.

Preferably the elastic web material is stretched to a length which exceeds its untensioned length with at least 20% and more preferably at least 30% while being joined to the substantially non-elastic web materials.

In a further aspect of the disclosure a pair of continuous lengths of said substantially non-elastic web material intended to form the waistband are fed substantially in parallel in said feeding direction (A) and spaced apart a selected distance, said substantially non-elastic web materials each having two longitudinal side edges. A pair of continuous lengths of said elastic web material intended to form at least part of the front panel and the back panel respectively are fed substantially in parallel and spaced apart a selected distance in said feeding direction (A), said elastic web materials each having two longitudinal side edges.

Each of said substantially non-elastic web materials are brought to overlap a selected distance at their longitudinal edges facing each other, with a respective elastic web material and said overlapping side edges are joined with each other. A continuous length of a substantially non-elastic. web material intended to form a crotch portion web material is fed in said feeding direction (A) between said pair of elastic web materials, wherein the crotch portion web material has a pair of longitudinal side edges and is at its longitudinal side edges joined in an overlapping manner to the respective longitudinal side edges of the elastic web materials. Each of said elastic web materials is stretched to a length which exceeds its untensioned length with at least 10% while being joined to the substantially non-elastic crotch portion web material.

BRIEF DESCRIPTION OF DRAWINGS

Embodiments of the invention will be described in the following in greater detail by way of example and with reference to the accompanying drawings, in which.

DESCRIPTION OF PREFERRED EMBODIMENTS

Figure 1:
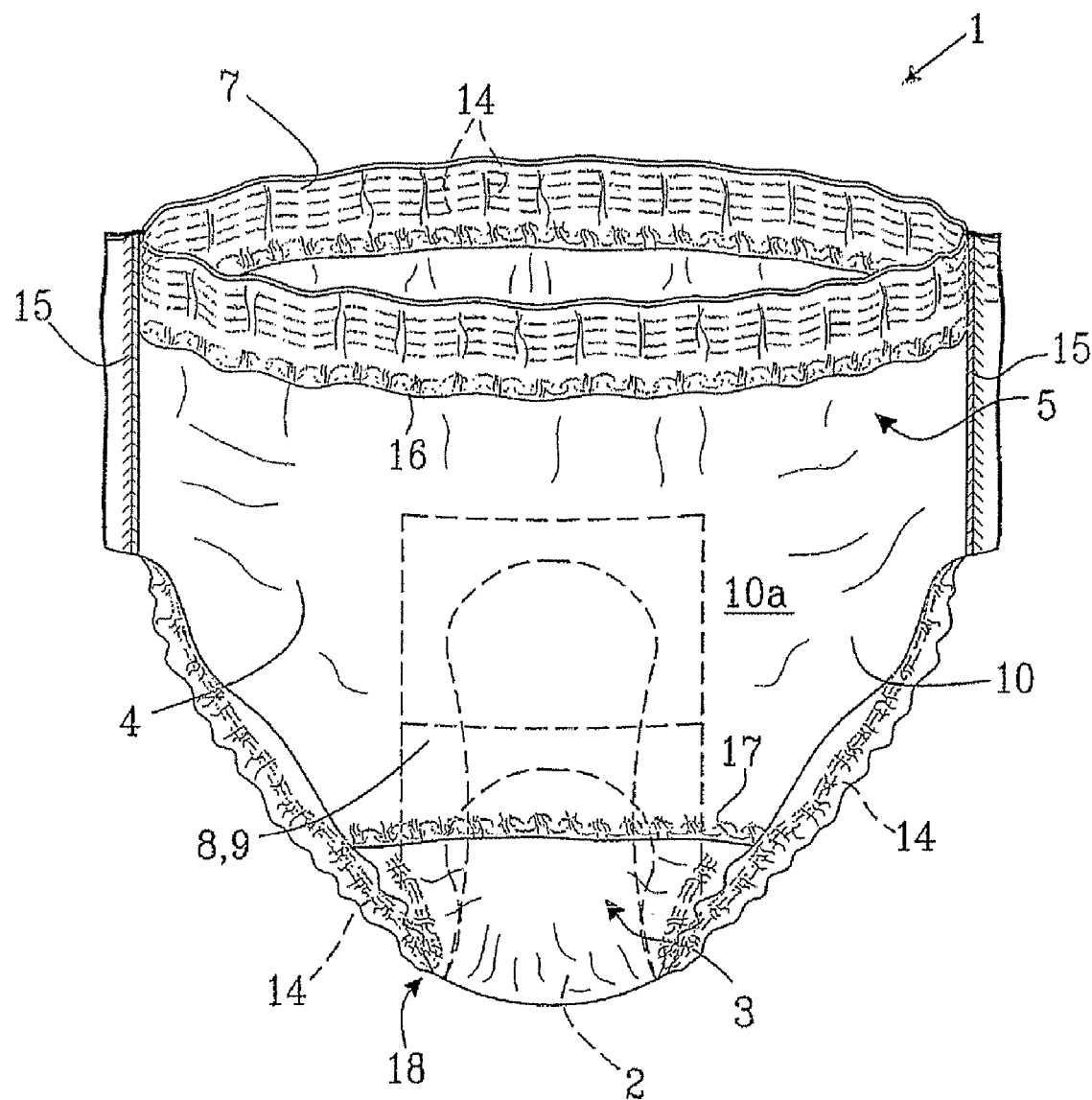
FIG. 1 shows a perspective view of a pant diaper.

Embodiments of the invention will in the following be closer described with reference to some embodiments shown in the accompanying drawings.

Absorbent Article

The term "absorbent article" refers to products that are placed against the skin of the wearer to absorb and contain body exudates, like urine, faeces and menstrual fluid. The invention mainly relates to disposable absorbent articles, which means articles that are not intended to be laundered or otherwise restored or reused as an absorbent article after use. Pant-type absorbent articles are referred to having a core region and a chassis region surrounding the core region. Examples of such pant-type absorbent articles are pant diapers, sanitary pants and incontinence pants.

The drawings show an embodiment of a pant diaper 1 for an infant or an incontinent adult. Said pant diaper typically comprises an absorbent core 2 located in a core region 3 of the article, and a chassis 4 surrounding the core region. The chassis comprises a front panel 5, a back panel 6 and an elastic waist band 7. The core region 3 is located at least in the crotch portion 19 of the article and extends a certain distance into the front 5 and back panels 6. The crotch portion 19 is herewith defined as the narrow part of the article intended to be worn in the wearer's crotch between the legs.

The article has a longitudinal direction y and a transverse direction x.

The article comprises a liquid permeable topsheet 8 and a liquid impermeable backsheet 9 covering at least the core region 3. The absorbent core 2 is enclosed between the topsheet 8 and the backsheet 9.

Topsheet

The liquid permeable topsheet 8 can consist of a nonwoven material, e g spunbond, meltblown, carded, hydroentangled, wetlaid etc. Suitable nonwoven materials can be composed of natural fibers, such as woodpulp or cotton fibres, manmade fibres, such as polyester, polyethylene, polypropylene, viscose etc. or from a mixture of natural and manmade fibres. The topsheet material may further be composed of tow fibres, which may be bonded to each other in a bonding pattern, as e.g. disclosed in EP-A-1 035 818. Further examples of topsheet materials are porous foams, apertured plastic films etc. The materials suited as topsheet materials should be soft and non-irritating to the skin and intended to be readily penetrated by body fluid, e.g. urine or menstrual fluid. The topsheet may be different in different parts of the absorbent article.

Backsheet

The liquid impervious backsheet 9 covering the core region 3 on the garment-facing side of the core is of a liquid impervious material, such as a thin plastic film, e.g. a polyethylene or polypropylene film, a nonwoven material coated with a liquid impervious material, a hydrophobic nonwoven material, which resists liquid penetration or a laminate comprising plastic films and nonwoven materials. The core region backsheet material 9 may be breathable so as to allow vapour to escape from the absorbent core, while still preventing liquids from passing therethrough. Examples of breathable backsheet materials are porous polymeric films, nonwoven laminates from spunbond and meltblown layers, laminates from porous polymeric films and nonwovens. The backsheet 9 is preferably inelastic.

Elastic Web Material

The outer coversheet covering the front and back panels 5 and 6 of the chassis 4 comprises an elastic web material 10, which is elastic at least in the transverse x-direction of the article. The elasticity in the x-direction should be at least 30%, preferably at least 50%, more preferably at least 70%, as measured by the elasticity test specified below.

Preferably the elastic web material is elastic also in the y-direction of the article. However the elasticity in the y-direction is preferably lower than in the x-direction. The elasticity in the y-direction should in be at least 20%.

In the embodiment shown and described below the elastic web material is an elastic laminate 10 composed of first and second outer layers of fibrous material 11 and 12 and a middle elastic film layer 13 located between said fibrous layers. However it is understood that other types of elastic web materials may be used, such as elastic nonwoven materials, nonwoven materials which per se are inelastic, but which have been elastified by means of elastic threads etc. The elastic web materials may comprise one layer or two or more layers that have been laminated.

In the elastic laminate shown and described below it is preferred that the outer fibrous layers 11 and 12 are chosen so that they, in combination with the inner elastic film layer 13, give the material high resistance to puncture. They also provide a soft and cloth-like feel to the laminate. Examples of suitable materials are carded webs and spunbond materials. The basis weight of the fibrous material layers should be between 10 and 35 $g/m^2$, preferably between 12 and 30 $g/m^2$, more preferably between 15 and 25 $g/m^2$. Examples of suitable polymers used in the fibrous materials are polyethylene, polyesters, polypropylene and other polyolefin homopolymers and copolymers. Natural fibres, for example cotton, may also be used as long as they provide the required properties. A mixture of polymers can contribute to a higher flexibility of the nonwoven layer, and through this, give the nonwoven material a higher elongation at maximum load. A mixture of polyethylene and polypropylene polymers has proved to provide good results in this respect. A mixture of fibers of different polymers is also possible.

The middle layer 13 is according to one embodiment of the invention an apertured elastic film having a basis weight between 20 and 80 $g/m^2$, preferably between 20 and 60 $g/m^2$. The film may be of any suitable elastic polymer, natural or synthetic. Some examples of suitable materials for the elastic film are low crystallinity polyethylenes, metallocene-catalyzed low crystallinity polyethylene, ethylene vinyl acetate copolymers (EVA), polyurethane, polyisoprene, butadiene-styrene copolymers, styrene block copolymers, such as styrene/isoprene/styrene (SIS), styrene/butadiene/styrene (SBS), or styrene/ethylene-butadiene/styrene block copolymer. Blends of these polymers may also be used as well as other modifying elastomeric or non-elastomeric materials. One example of a suitable film is an apertured three-layer elastomeric film of PE-SEBS-PE.

The total basis weight of the laminate is preferably 100 $g/m^2$ or less, more preferably no more than 90 $g/m^2$.

The elastic laminate 10 may be manufactured according to the method disclosed in WO 03/047488, wherein one spunbond layer 11 is applied to the film 13 in a tacky state and will thus bond to the film layer, while the other spunbond layer 12 is adhesively laminated to the film layer 13, using for example a pressure sensitive hot melt adhesive. Alternatively the laminate is manufactured according to a modified version of this known method, wherein the modification involves that the laminate is incrementally stretched (through intermeshing gears, IMG), to a point below the elongation at peak load of at least one of the non-elastic nonwoven layers to retain some strength for at least one of the nonwoven layers. The other layer may also be stretched to a point below its elongation at peak load, or to a point at which it will tear during stretching.

The method disclosed in WO 03/047488 involves stretching of the laminate above the point of failure of the fibrous material, so that the non-elastic layers break completely. Therefore, as described in WO 03/047488, the elongation of the laminate is not limited by the stretch modulus of the non-elastic material.

In a preferred embodiment at least one, preferably both fibrous layers, which are bound to the elastic film, are not, in contrast to the method described in WO 03/047488, completely torn upon manufacture of a laminate according to the present invention. Selection of fibrous materials which have an elongation at maximum load greater than the elasticity of the elastic laminate allows the elastic film to stretch without being hindered by the fibrous layers. Such a selection also ensures that the fibrous layers contribute to the puncture resistance of the laminate, as they are not completely torn or broken during manufacture. Preferably both fibrous layers or at least one of the fibrous layers have an elongation at maximum load that is at least 10% higher than the elasticity of the laminate. This is described in more detail in PCT/SE2004/001005, which is incorporated herein by reference.

The opacity of a material layer is the characteristic ability of the material layer to visually hide from view an underlying object or pattern. The opacity is measured in %, wherein 100% opacity means that nothing can be seen through the material layer and 0% means that the material layer is completely transparent. The opacity is measured by the Opacity Test described below, which is based on luminous-reflectance-factor data.

Opacity of the laminate can be obtained by the incorporation of opacifying fillers into the laminate, particularly into the elastic film. Such pigments can be organic or inorganic dyes, colouring agents, or whitening agents. Inorganic materials such as titanium dioxide, inorganic carbonates, synthetic carbonates, talc, nepheline syenite, magnesium hydroxide, aluminium trihydrate siatomaceous earth, mica, natural or synthetic silicas, calcinated clays and mixtures thereof are preferred examples of opacifying fillers.

The filler is preferably added as a master batch at the extrusion of the film. One example of an appropriate concentration is about 5% filler by weight of the film.

It is further preferred that the elastic laminate 10 has a breathability (Water Vapour Transmission Rate) according to ASTM E96-00 Procedure D of at least 1500 g/m$^2$ 24 h, preferably at least 3000 g/m$^2$ 24 h.

The open area of the elastic film layer is preferably at least 8%, more preferably at least 10%. The open area is measured by image analysis methods and is defined as the sum of the hole area divided by the total area of the film sample.

Absorbent Core

The "absorbent core" is the absorbent structure disposed between the two covers of the absorbent article. The absorbent core 2 can be of any conventional kind. Examples of commonly occurring absorbent materials- are cellulosic fluff pulp, tissue layers, highly absorbent polymers (so called superabsorbents), absorbent foam materials, absorbent nonwoven materials or the like. It is common to combine cellulosic fluff pulp with superabsorbent polymers in an absorbent core. Superabsorbent polymers are water-swellable, water-insoluble organic or inorganic materials capable of absorbing at least about 20 times its weight and in an aqueous solution containing 0.9 weight percent of sodium chloride. Organic materials suitable for use as a superabsorbent material can include natural materials such as polysaccharides, polypeptides and the like, as well as synthetic materials such as synthetic hydrogel polymers. Such hydrogel polymers include, for example, alkali metal salts of polyacrylic acids, polyacrylamides, polyvinyl alcohol, polyacrylates, polyacrylamides, polyvinyl pyridines, and the like. Other suitable polymers include hydrolyzed acrylonitrile grafted starch, acrylic acid grafted starch, and isobutylene maleic anhydride copolymers and mixtures thereof. The hydrogel polymers are preferably lightly crosslinked to render the material substantially water insoluble. Preferred superabsorbent materials are further surface crosslinked so that the outer surface or shell of the superabsorbent particle, fiber, flake, sphere, etc. possesses a higher crosslink density than the inner portion of the superabsorbent. The superabsorbent materials may be in any form suitable for use in absorbent composites including particles, fibers, flakes, spheres, and the like.

A high absorption capacity is provided by the use of high amounts of superabsorbent material. For an absorbent core comprising a matrix of hydrophilic fibers, such as cellulosic fibers, and superabsorbent material, the proportion of superabsorbent material is preferably between 10 and 90% by weight, more preferably between 30 and 70% by weight.

It is conventional in absorbent articles to have absorbent cores comprising layers of different properties with respect to liquid receiving capacity, liquid distribution capacity and storage capacity. The thin absorbent bodies, which are common in for example baby diapers and incontinence guards, often comprise a compressed mixed or layered structure of cellulosic fluff pulp and superabsorbent polymers. The size and absorbent capacity of the absorbent core may be varied to be suited for different uses such as for infants or for adult incontinent persons.

The absorbent core may further include an acquisition distribution layer placed on top of the primary absorbent body and which is adapted to quickly receive and temporarily store discharged liquid before it is absorbed by the primary absorbent core. Such acquisition distribution layers are well known in the art and may be composed of porous fibrous waddings or foam materials.

Pant Diaper

The pant diaper disclosed in FIG. 1 is intended to enclose the lower part of the wearer's trunk like a pair of underwear pants. It comprises a core region 3 located in the narrow crotch portion 19 of the article and extending into the front 5 and back panels 6 of the absorbent pants. A chassis region 4 surrounds the core region 3. The core region 3 is defined as the surface area of the article which is occupied by the absorbent core 2 and the areas outside the core, which are covered by the liquid-impervious backsheet 9. The chassis 4 comprises a front panel 5, a back panel 6 and an elastic waist band 7 secured to the front and back panel. In an alternative embodiment only one of the front 5 and back panels 6 have an elastic waist band 7 secured thereto. Each of the front and back panels 5 and 6 has a waist edge 5a and 6a, a crotch edge 5b and 6b, and a pair of side edges 5c, 6c and 5d and 6d respectively. The front 5 and back panels 6 are joined to each other along their side edges 5c, 6c and 5d, 6d by ultrasonic welds 15, glue strings or the like to form side seams. The elastic waist band portions 7 secured to the front panel 5 and the back panel 6, respectively, are also joined to each other along said side seams. The joined front and back panels 5 and 7 and waist band portions 7 define the waist opening and a pair of leg openings of the pant diaper.

Figure 2:
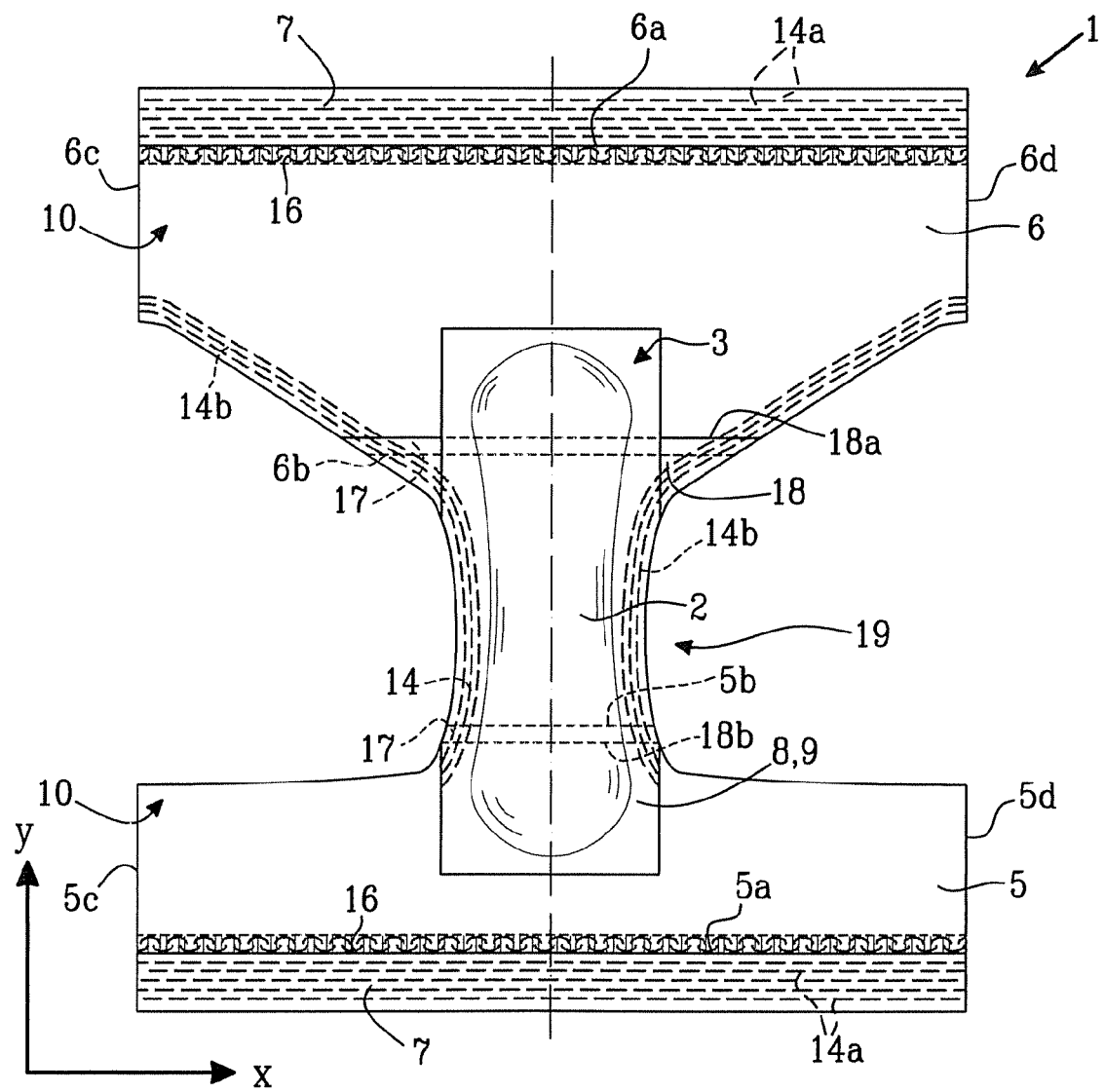
FIG. 2 shows is a plan view of the pant diaper in its flat, uncontracted state prior to formation as seen from the body facing side.

According to one embodiment of the invention the surface area of the absorbent core 2 amounts to no more than 30% of the total surface area of the article, preferably no more than 20%, as measured in a flat state of the article. The term "flat state" herein means in an opened untensioned state, as seen in FIG. 2, and in which any tensioned elastic members have been deactivated.

The elastic web material 10 may cover the entire article, including the core region 3 and the entire chassis region 4. However according to a preferred embodiment a substantial part of the crotch portion 19 of the article is free from the elastic web material 10. A "substantial part" used herein refers to at least 50%, preferably at least 75%.

A crotch panel 18, which preferably is a non-elastic material, more preferably a non-elastic nonwoven material, is arranged in the crotch portion of the article and overlaps with the elastic front and back panels 5 and 6. The crotch panel 18 is along its transverse side edges 18a and b joined in an overlapping manner to the front and back panels 5 and 6 respectively by means of ultrasonic welds 17, glue strings or the like.

The elastic waist band 7 comprises a substantially non-elastic nonwoven material 22 that is elasticized by elongate elastic members 14a, such as elastic threads, contractably affixed between material layers, such as nonwoven materials. Elastic threads 14b may also be arranged around the leg openings of the article.

Figure 5:
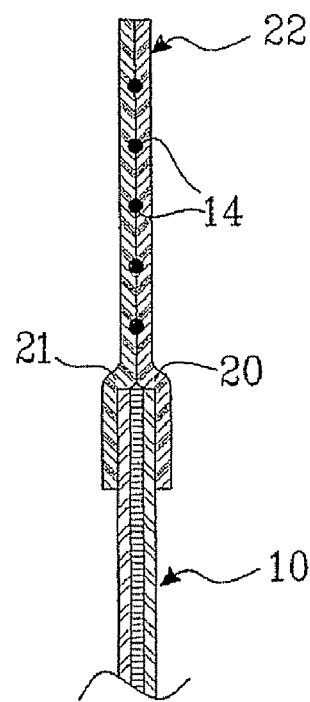
FIG. 5 is a cross section according to the line V-V in FIG. 4.
Figure 6:
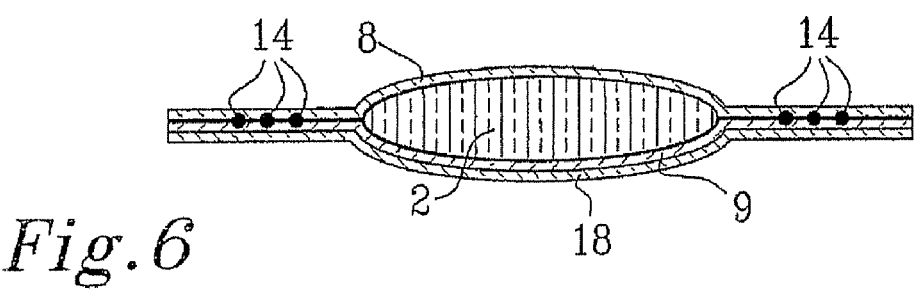
FIG. 6 is a cross section according to the line VI-VI in FIG. 3.
Figure 7:
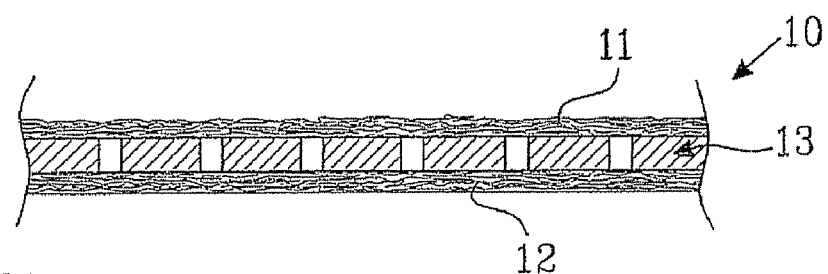
FIG. 7 is a cross section through an elastic laminate according to the line VII-VII in FIG. 3.

The elastic waistband 7 comprises first and second plies 20 and 21 of substantially non-elastic web material enclosing between them at least one elastic thread 14 and preferably two or more elastic threads. The substantially non-elastic web material is preferably a nonwoven, The first ply 20 of the waist band is secured to the body-facing side of the elastic web material 10 at the waist edges 5a and 6a of the front and back panels 5 and 6 respectively, and the second ply 21 of the waist band is secured to the opposite, outer side of the elastic web material 10 just opposite the first ply 20. This is best illustrated in FIG. 5.

Figure 4:
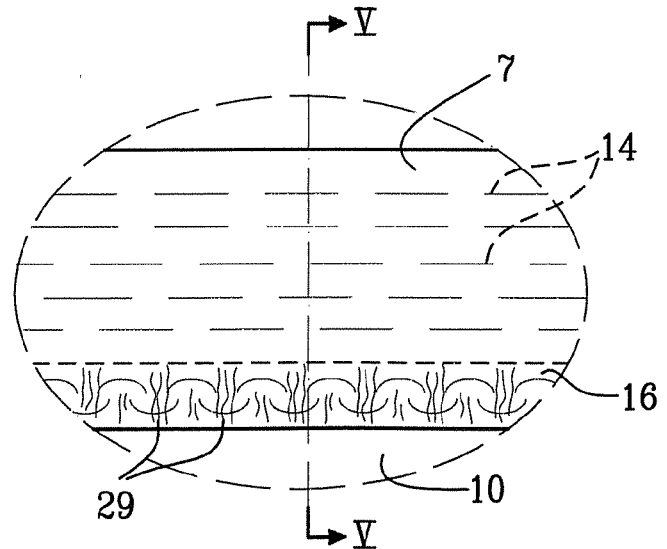
FIG. 4 is a plan view of a part of the waist area in flat, untensioned state, in which the waist elastic members have been deactivated and the elastic web material is in a relaxed, untensioned condition.

The first and second plies 20 and 21 are secured to the elastic web material 10 while this is in a stretched condition. The first and second plies 20 and 21 with the elastic web material 10 held there between form a waistband seam 16 joined by ultrasonic welding, glue strings or the like while holding the elastic web material in a stretched condition. This will result in that the first and second plies of non-elastic material 20 and 21 form gathers 29 along the waistband seam 16 when the elastic web material 10 is in a relaxed position. This is illustrated in FIG. 4 showing the elastic threads 14a of the waistband 7 in a deactivated state and the elastic web material 10 is in a relaxed, untensioned condition.

The elastic waistband 7 is preferably formed from a double folded substantially non-elastic web material 22, however may also be formed from two separate plies 20, 21 which are joined together to enclose therebetween the elastic threads 14.

The waistband seam 16 thus formed provides a very smooth joint between the front and back panels 5, 6 and the waist band 7 both on the wearer facing surface and on the opposite, outer, surface of the article. No chafing or ugly joint edges appear on any side, inner or outer, of the article, since only one single ply of web material is joined to each side of the inner elastic web material 10 in the waistband seam 16, as best illustrated in FIG. 5. The waistband seam 16 will further have a certain degree of elasticity.

In an alternative embodiment only one of the front and back panels 5 and 6 is joined to an elastic waistband 7, wherein the elasticity of the elastic web material 10 is sufficient to keep the other panel in place above the hips of the wearer.

Figure 3:
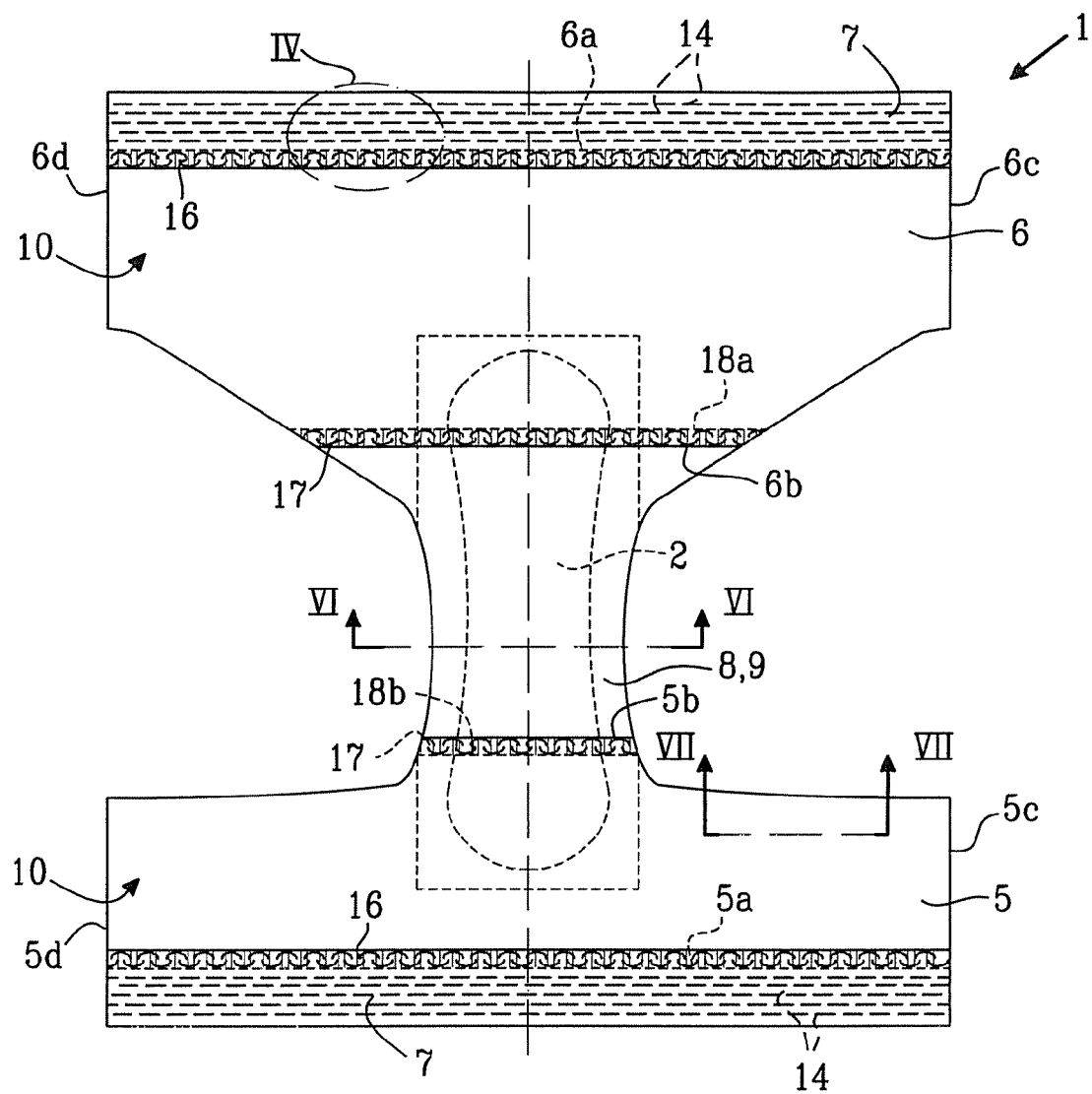
FIG. 3 is a corresponding plan view from the opposite, outer side of the pant diaper.

The liquid-impervious backsheet material 9 underlies the absorbent core 2 and adjacent areas immediately outside the absorbent core 2. The area covered by the liquid-impervious backsheet 9 is defined as the core region 3. The crotch nonwoven material 18 is arranged on the garment-facing side of the liquid-impervious backsheet 9 in the crotch portion of the article. The core region 3 extends into the front and back panels 5 and 6 so that the elastic web material 10 and the liquid impervious backsheet overlap in the outer parts of the core region 3, as seen in FIGS. 2 and 3, wherein the elastic web material 10 is arranged on the garment facing side of the liquid impervious backsheet 9.

The elastic web material constitutes the sole component of parts of the front and back panels 5 and 6 of the chassis 4. In at least 20%, preferably at least 25%, more preferably at least 30% and most preferably at least 40% of the total surface area of the article, as seen in a flat state according to FIGS. 2 and 3, the elastic web material 10 constitutes the sole component of the chassis.

No additional elasticized side panels joining the front and back panels 5 and 6 are needed when using the elastic web material 10 according to the invention. If desired, additional elasticized side panels may of course be provided, especially in cases where the elastic web material 10 is arranged only in parts of the front and/or back panels.

As stated above the elastic web material 10 has an opacity of at least 40%, preferably at least 50% and more preferably at least 60%. The opacity of the elastic web material provides a cloth-like appearance to the article, which is of particular importance when the article is a pant diaper. Especially in this case, where the elastic web material forms the sole component in considerable surface area regions of the pant diaper, such as large areas of the front and back panels, and the absorbent core covers only relatively small areas, 30% or less, of the article, the appearance of the elastic web material is of great importance for the overall appearance of the article. Thus by making the elastic web material opaque with an opacity of at least 40%, the pant diaper will appear more cloth-like and more like "normal" underwear, than if the elastic web material would have a higher degree of transparency. The opacity is measured by the Opacity Test disclosed in PCT/SE2004/001415.

It is further desired that the elastic web material has a puncture resistance of at least 15N as measured according to ASTM Designation D3763-02. Preferably, the elastic web material of the present invention has a puncture resistance of at least 20N, and more preferably at least 30N.

The elastic web material should preferably have a softness according to Kawabata of at least 20, preferably at least 30 and most preferably at least 40. It is further desired that it has a formability according to Kawabata of no more than 50, preferably no more than 30, more preferably no more than 20 and most preferably no more than 10. It is also desired that the elastic web material has a drapability according to Kawabata of no more than 40. The softness, formability and drapability according to kawabata are measured according to the test methods given in PCT/SE2004/001004.

Elasticity Test

The method measures how an elastic material behaves at repeated load and unload cycles. The sample is stretched to a predetermined elongation and a cyclic movement between 0 and said predetermined elongation is performed. Desired load and unload forces are recorded. The permanent, i.e. remaining, elongation of the relaxed material is measured.

A tensile tester, Lloyd LRX, able to perform cyclic movements and equipped with a printer/plotter or software presentation is used. The sample is prepared by cutting it to a width of 25 mm and a length that is preferably 20 mm longer than the distance between the clamps in the tensile tester.

The tensile tester is calibrated according to the apparatus instructions. The parameters needed for the test (load and unload forces) are adjusted to:

| | |
|---|---|
| Crosshead speed: | 500 mm/min |
| Clamp distance: | 50 mm |
| Preload: | 0.05 N |

The sample is placed in the clamps according to the marks and it is made sure that the sample is centered and fastened perpendicularly in the clamps. The tensile tester is started and three cycles between 0 and the predetermined elongation, equal to the highest defined $1^{st}$ load, are performed. Before the last cycle, the sample is relaxed for 1 minute, then the permanent elongation is measured by stretching the sample until a force of 0.1 N is detected and the elongation is read.

The permanent elongation after relaxation should be less than 10% and is measured by the method above. Thus an elasticity of 30% is defined as that the laminate should have a permanent relaxation after elongation of less than 10% after being exerted to an elongation of 30% in the tensile tester above. An elongation of 30% means an elongation to a length that is 30% longer than the initial length of the sample.

Manufacturing Process

Figure 8:
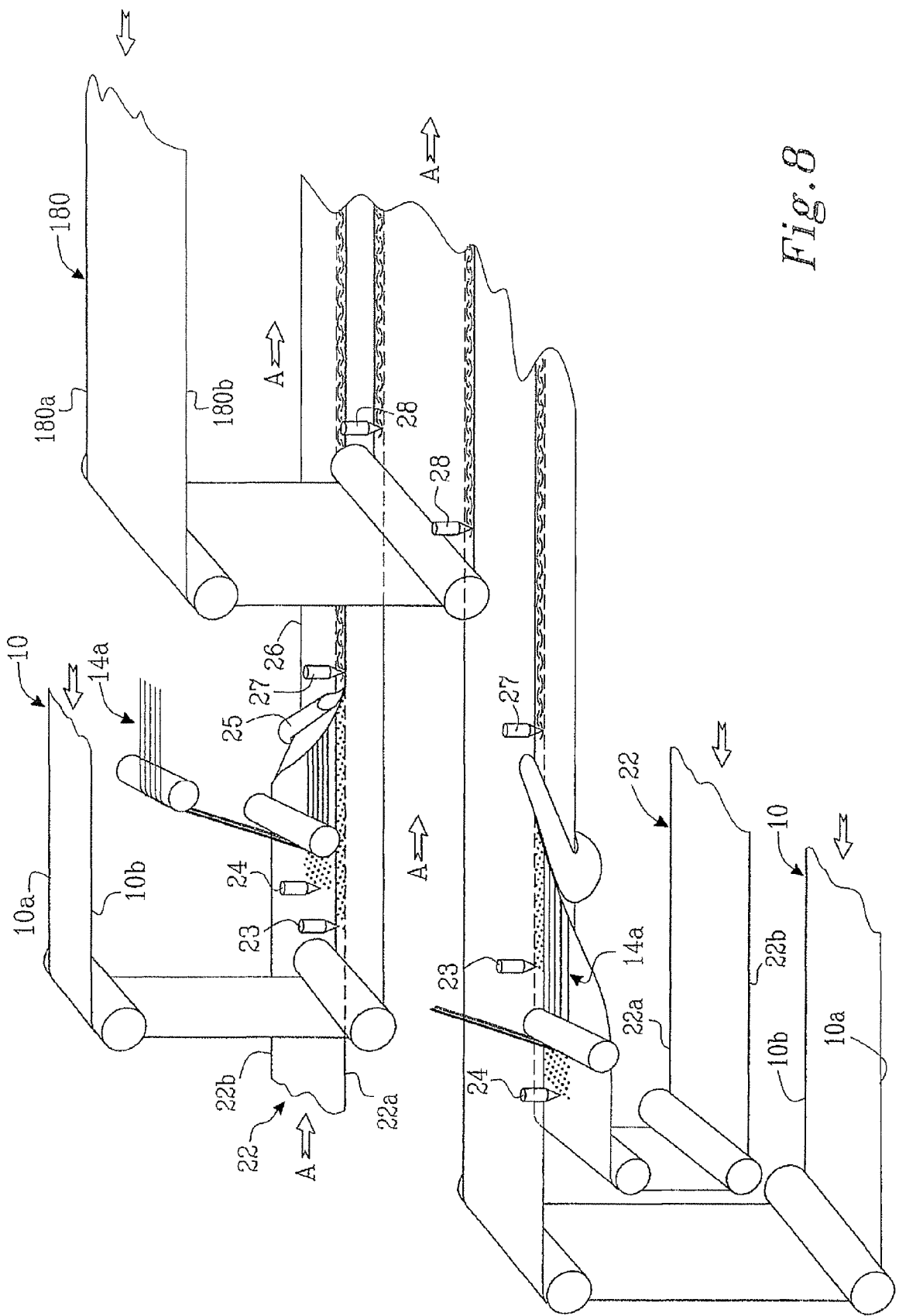
FIG. 8 is a schematic perspective view of a length of a production line for joining an elastic waistband to the front and back panels of a pant article according to the invention.

The pant diaper may be manufactured by a process which is illustrated in FIG. 8. The various components of the absorbent article are united on a (not shown) conveyor belt running in a direction of travel denoted by arrow A. A pair of continuous lengths of substantially non-elastic web material 22 intended to form the waistband 7, are fed in parallel and spaced apart a selected distance along the conveyor belt. The non-elastic web materials 22 have two longitudinal side edges 22a and b and are along their longitudinal edges 22a facing each other brought together with a pair of continuous lengths of the elastic web material 10 intended to form the front panel 5 and the back panel 6 respectively. The elastic web material 10 has two longitudinal side edges 10a and b. The non-elastic and elastic web materials 22 and 10 are brought together and joined in an overlapping manner, so that the their respective longitudinal side edges 10 and 22a overlap at least about 5 mm and preferably no more than 20 mm. The elastic web materials 10 are supplied in a selectively stretched condition while being secured to the non-elastic webs 22. The elastic webs 10 are stretched to a length which exceeds their untensioned length with at least 10%, preferably at least 20% and more preferably at least 30%. The overlapping edges of the non-elastic web 22 and the elastic web 10 are joined together by gluing, ultrasonic welding or the like by a device denoted with the numeral 23. The non-elastic web materials 22 overlap with the elastic web materials 10 on the underside thereof according to FIG. 8. The free longitudinal edges 10b of the two elastic web materials 10 are spaced apart a selected distance adapted to accommodate the crotch web material 18 there between.

A plurality of elongate elastic members 14a are then supplied and joined to each of the non-elastic web materials 22 in any suitable manner known in the art, for example by gluing 24. The elongate elastic members 14a are supplied in a selectively tensioned manner or they may alternatively be supplied in a substantially untensioned manner and subsequently be activated to tensioned state, for example by heat. In the latter case the elongate elastic members 14a are of a specific type of elastomeric material, referred to as a heat-elasticizable material.

After supplying the elongate elastic members 14a to the non-elastic web materials 22, said web materials pass through a folding board 25 each, which continuously folds the respective non-elastic web material 22 transversely to the feeding direction A along a fold line 26 and over the elongate elastic members 14. The free longitudinal edge 22b of each non-elastic web material 22 is subsequently secured to the respective elastic web material 10 to its longitudinal edge 10a in an overlapping manner on the opposite side thereof (the upper side according to FIG. 8) as the other longitudinal edge 22a of non-elastic web material, which has already been secured to the elastic web material 10. The joining of the overlapping edges of non-elastic web 22 and elastic web 10 is made by gluing, ultrasonic welding or the like by a device denoted with the numeral 27.

The elastic laminate 10 is held in continued selectively stretched condition through the joining device 27 as described above. The joining effect, for example the ultrasonic weld, provided by the second joining device 27 may be considerably stronger than the joining effect provided by the first joining device 23, which may only provide for example a slight tack weld sufficient to keep the overlapping edges of the two material webs 10 and 22 together to the next joining station 27. The folded non-elastic web material 22, with the elongate elastic members 14 enclosed therein, will form the elastic waistband 7 of the absorbent article.

Alternatively to folding the non-elastic web material 22, a further non-elastic web material may be supplied and joined in an overlapping manner to the longitudinal edge 10a of the elastic laminate 10 at an opposite side thereof with respect to the first non-elastic web material 22, while the elastic web material is held in said stretched condition. The free side edges of the two non-elastic web materials are joined to each other either in a preceding or subsequent step. In this case each of the non-elastic web materials 22 are of a width corresponding to the width of the waistband 7.

In a next station a continuous length of second substantially non-elastic web material 180 intended to from the crotch panel 18 is supplied and is at its longitudinal side edges 180a and b joined to the longitudinal edges 10b of the elastic web material 10. The crotch panel web material 180 and the elastic web materials 10 are joined in an overlapping manner by gluing, ultrasonic welding or the like by a joining device 28 in a manner as disclosed above. Preferably the elastic web materials 10 are kept in their selectively stretched condition as described above, i.e. stretched to a length which exceeds their untensioned length with at least 10%, preferably at least 20% and more preferably at least 30%, while being joined to the crotch panel web material 180. The elastic webs 10 with the waistbands 7 joined thereto and the crotch panel web material 180 form a production web which is processed further to form the pant article.

Said production web thus is formed from different material webs joined together in different process steps, wherein the elastic web 10 is joined to the substantially inelastic web materials 22 and 180 in a selectively stretched and elongated condition. Certain width variations of this selectively stretched elastic web 10 may occur through the process, however such width variations can be compensated for since the joining of the elastic web 10 to the substantially non-elastic webs 22 and 180 takes place in several different process steps.

It is understood that the different process steps of joining the different material webs 10, 22 and 180 may take place in any order.

In subsequent steps (not shown) the core region 3 comprising the absorbent core 2 and the topsheet 8 and backsheet 9 is attached at spaced intervals to the production web formed by the crotch portion web material 180 and elastic web materials 10. Further components like elongate elastic members forming leg elastics are attached to the production web in a suitable manner known in the art. Leg openings are cut in the production web and the pant diaper is formed by folding the production web in double in the production direction, joining the folded production web, for example by ultrasonic welding, intermittently transverse to the feeding direction from the waist opening to the leg openings to form side seams and subsequently cutting along the side seams to form separate pant articles.

It is understood that although the invention has been described with reference to preferred embodiments, several modifications are possible within the scope of the claims, and equivalents thereof. The invention therefore intends to cover any variations or equivalents which are within known or customary practice within the technical field to which it belongs.

What is claimed is:

1. A pant-type absorbent article, said article comprising a core region comprising an absorbent core and a chassis, said chassis comprising a front panel, a back panel and an elastic waistband, each of the front and back panels having a waist edge, a crotch edge and a pair of side edges wherein the front and back panels are joined to each other along two opposite side edges to define a waist-opening and a pair of leg-openings, at least one of the front and back panels comprises an elastic web material constituting the sole component of at least part of the front and/or back panels, the elastic waistband being joined to the waist edge of at least one of the front and back panels, wherein the elastic waistband comprises a first ply and a second ply of substantially non-elastic web material enclosing between them at least one elongate elastic member, said article having a longitudinal and a transverse direction, said first ply of substantially non-elastic web material being secured to one side of said elastic web material at the waist edge of at least one of the front and back panels and said second ply of substantially non-elastic web material being secured to the opposite side of said elastic web material just opposite said first ply, the first and second plies being secured to the elastic web material while the elastic web material is in a stretched condition having a length which exceeds at least 10% of its untensioned length, the first and second plies of substantially non-elastic web material with said elastic web material held there between forming a waistband seam, wherein the first and second plies of substantially non-elastic material form gathers along said waistband seam when said elastic web material is in a relaxed position.

2. The pant-type absorbent article as claimed in claim 1, wherein said elastic waistband is formed from a folded substantially non-elastic web material so as to form said first and second plies enclosing said at least one elongate elastic member.

3. The pant-type absorbent article as claimed in claim 1, wherein said elastic web material constitutes the sole component of the chassis in at least 20% of the total surface area of the article.

4. The absorbent article as claimed in claim 1, wherein the elastic web material is a laminate composed of first and second layers of fibrous material and an elastic film layer located between said first and second fibrous layers.

5. The absorbent article as claimed in claim 4, wherein said elastic laminate has a Water Vapour Transmission Rate according to ASTM E96-00 Procedure D of at least 1500 g/m² 24h.

6. The absorbent article as claimed in claim 4, wherein said elastic laminate comprises first and second fibrous layers of spunbond material, each having a basis weight of between 10 and 35 g/m², and a breathable elastic film layer having a basis weight between 20 and 80 g/m², said elastic laminate having a Water Vapour Transmission Rate according to ASTM E96-00 Procedure D of at least 1500 g/m² 24h.

7. The absorbent article as claimed in claim 1, the elastic web material constitutes the sole component of the chassis in at least 25% of the total surface area of the article.

8. The absorbent article as claimed in claim 1, wherein said elastic web material has an elasticity in the transverse direction of the article of at least 30% when measured according to the elasticity test specified in the description.

9. The absorbent article as claimed in claim 1, wherein a crotch panel of a substantially inelastic web material is arranged in the crotch portion of the article, said crotch panel being joined to the front and back panels comprising said elastic web material.

10. A pant-type absorbent article, said article comprising a core region comprising an absorbent core and a chassis, said chassis comprising a front panel, a back panel and an elastic waistband, each of the front and back panels having a waist edge, a crotch edge and a pair of side edges wherein the front and back panels are joined to each other along two opposite side edges to define a waist-opening and a pair of leg-openings, at least one of the front and back panels comprises an elastic web material constituting the sole component of at least part of the front and/or back panels, the elastic waistband being joined to the waist edge of at least one of the front and back panels, wherein the elastic waistband comprises a first ply and a second ply of substantially non-elastic web material enclosing between them at least one elongate elastic member, said article having a longitudinal and a transverse direction, said first ply of substantially non-elastic web material being secured to one side of said elastic web material at the waist edge of at least one of the front and back panels and said second ply of substantially non-elastic web material being secured to the opposite side of said elastic web material just opposite said first ply, the first and second plies being secured to the elastic web material while the elastic web material is in a stretched condition, the first and second plies of substantially non-elastic web material with said elastic web material held there between forming a waistband seam, wherein the first and second plies of substantially non-elastic material form gathers along said waistband seam when said elastic web material is in a relaxed position, and wherein the surface area of the absorbent core amounts to no more than 30% of the total surface area of the article, as measured in a flat state of the article.

11. A method for joining a separate elastic waistband to a pant-type absorbent article as claimed in claim 1, wherein the elastic waistband comprises a first ply and a second ply of substantially non-elastic web material enclosing between them at least one elongate elastic member and said first and second plies of substantially non-elastic web material are joined to an elastic web material constituting a component of at least part of the front and/or back panels of the article, the method comprising:

feeding said elastic web material and said substantially non-elastic web material substantially in parallel in a feeding direction, each of said web materials having a pair of longitudinal side edges, said elastic web material being fed in a selectively stretched condition;

bringing a first longitudinal side edge of the elastic web material to overlap a selected distance with a first longitudinal side edge of the substantially non-elastic web material and joining said overlapping side edges to each other, wherein said elastic web material is stretched to a length which exceeds its untensioned length by at least 10% while being joined to the substantially non-elastic web material;

providing at least one elongate elastic member and joining it to said substantially non-elastic web material;

folding the substantially non-elastic web material in a direction generally transverse to said feeding direction, over the at least one elongate elastic member, and joining the second longitudinal edge of the substantially non-elastic web material in an overlapping manner to the first longitudinal edge of the elastic web material at an opposite side thereof with respect to the first longitudinal edge of the substantially non-elastic web material, so that the first side edge of the elastic web material is held between the first and second side edges of the substantially non-elastic web material, wherein said elastic web material is stretched to a length which exceeds its untensioned length with at least 10% while being joined to the substantially non-elastic web material;

or alternatively to folding the substantially non-elastic web material, providing a further substantially non-elastic web material and joining it in an overlapping manner to the first longitudinal edge of the elastic web material at an opposite side thereof with respect to the first substantially non-elastic web material, while the elastic web material is held in said stretched condition, and joining the free side edges of the two substantially non-elastic web materials.

12. The method as claimed in claim 11, wherein an elastic waistband is joined to the second elastic web material in a manner as disclosed in claim 11.

13. The method as claimed in claim 11, further comprising:
feeding a pair of continuous lengths of said substantially non-elastic web material intended to form the waistband substantially in parallel in said feeding direction and spaced apart a selected distance, said substantially non-elastic web materials each having two longitudinal side edges;

feeding a pair of continuous lengths of said elastic web material intended to form at least part of the front panel and the back panel respectively substantially in parallel and spaced apart a selected distance in said feeding direction, said elastic web materials each having two longitudinal side edges;

bringing each of said substantially non-elastic web materials to overlap a selected distance at their longitudinal edges facing each other, with a respective elastic web material and joining said overlapping side edges with each other; and feeding a continuous length of a substantially non-elastic web material intended to form a crotch portion web material in said feeding direction between said pair of elastic web materials, said crotch portion web material having a pair of longitudinal side edges and is at its longitudinal side edges joined in an overlapping manner to the respective longitudinal side edges of the elastic web materials;

wherein each of said elastic web materials is stretched to a length which exceeds its untensioned length with at least 10% while being joined to the substantially non-elastic crotch portion web material.

14. The absorbent article as claimed in claim 4, wherein said elastic laminate has a Water Vapour Transmission Rate according to ASTM E96-00 Procedure D of at least 3000 g/m² 24h.

15. The absorbent article as claimed in claim 4, wherein said elastic laminate comprises first and second fibrous layers of spunbond material, each having a basis weight of between 15 and 25 g/m², and a breathable elastic film layer having a basis weight between 20 and 60 g/m², said elastic laminate having a Water Vapour Transmission Rate according to ASTM E96-00 Procedure D of at least 3000 g/m² 24h.

16. The absorbent article as claimed in claim 1, wherein the elastic web material has a basis weight of no more than 90 g/m².

17. The absorbent article as claimed in claim 6, the elastic web material constitutes the sole component of the chassis in at least 40% of the total surface area of the article.

18. The absorbent article as claimed in claim 1, wherein said elastic web material has an elasticity in the transverse direction of the article of at least 70%, when measured according to the elasticity test specified in the description.

19. A pant-type absorbent article, said article comprising a core region comprising an absorbent core and a chassis, said chassis comprising a front panel, a back panel and an elastic waistband, each of the front and back panels having a waist edge, a crotch edge and a pair of side edges wherein the front and back panels are joined to each other along two opposite side edges to define a waist-opening and a pair of leg-openings, at least one of the front and back panels comprises an elastic web material constituting the sole component of at least part of the front and/or back panels, the elastic waistband being joined to the waist edge of at least one of the front and back panels, wherein the elastic waistband comprises a first ply and a second ply of substantially non-elastic web material enclosing between them at least one elongate elastic member, said article having a longitudinal and a transverse direction, said first ply of substantially non-elastic web material being secured to one side of said elastic web material at the waist edge of at least one of the front and back panels and said second ply of substantially non-elastic web material being secured to the opposite side of said elastic web material just opposite said first ply, the first and second plies being secured to the elastic web material while the elastic web material is in a stretched condition, the first and second plies of substantially non-elastic web material with said elastic web material held there between forming a waistband seam, wherein the first and second plies of substantially non-elastic material form gathers along said waistband seam when said elastic web material is in a relaxed position, wherein said elastic web material has an elasticity in the transverse direction of the article of at least 30% when measured according to the elasticity test specified in the description, and wherein the surface area of the absorbent core amounts to no more than 20% of the total surface area of the article, as measured in a flat state of the article.

20. A method for joining a separate elastic waistband to a pant-type absorbent article, wherein the elastic waistband comprises a first ply and a second ply of substantially non-elastic web material enclosing between the first and second plies at least one elongate elastic member, and said first and second plies of substantially non-elastic web material are joined to an elastic web material constituting a component of at least part of the front and/or back panels of the article, the method comprising:
feeding said elastic web material and said substantially non-elastic web material substantially in parallel in a feeding direction, each of said web materials having a pair of longitudinal side edges, said elastic web material being fed in a stretched condition;

bringing a first longitudinal side edge of the elastic web material to overlap a distance with a first longitudinal side edge of the substantially non-elastic web material and joining said overlapping side edges to each other, wherein said elastic web material is stretched to a length which exceeds its untensioned length by at least 10% while being joined to the substantially non-elastic web material;

providing at least one elongate elastic member and joining it to said substantially non-elastic web material; and folding the substantially non-elastic web material in a direction generally transverse to said feeding direction, over the at least one elongate elastic member, and joining the second longitudinal edge of the substantially non-elastic web material in an overlapping manner to the first longitudinal edge of the elastic web material at an opposite side thereof with respect to the first longitudinal edge of the substantially non-elastic web material, so that the first side edge of the elastic web material is held between the first and second side edges of the substantially non-elastic web material, wherein said elastic web material is stretched to a length which exceeds its untensioned length with at least 10% while being joined to the substantially non-elastic web material.

21. A method for joining a separate elastic waistband to a pant-type absorbent article, wherein the elastic waistband comprises a first ply and a second ply of substantially non-elastic web material enclosing between the first and second plies at least one elongate elastic member, and said first and second plies of substantially non-elastic web material are joined to an elastic web material constituting a component of at least part of the front and/or back panels of the article, the method comprising:

feeding said elastic web material and said substantially non-elastic web material substantially in parallel in a feeding direction, each of said web materials having a pair of longitudinal side edges, said elastic web material being fed in a stretched condition;

bringing a first longitudinal side edge of the elastic web material to overlap a distance with a first longitudinal side edge of the substantially non-elastic web material and joining said overlapping side edges to each other, wherein said elastic web material is stretched to a length which exceeds its untensioned length by at least 10% while being joined to the substantially non-elastic web material;

providing at least one elongate elastic member and joining it to said substantially non-elastic web material; and providing a further substantially non-elastic web material and joining it in an overlapping manner to the first longitudinal edge of the elastic web material at an opposite side thereof with respect to the first substantially non-elastic web material, while the elastic web material is held in said stretched condition, and joining the free side edges of the two substantially non-elastic web materials.

22. A method for joining a separate elastic waistband to a pant-type absorbent article, wherein the elastic waistband comprises a first ply and a second ply of substantially non-elastic web material enclosing between the first and second plies at least one elongate elastic member, and said first and second plies of substantially non-elastic web material are joined to an elastic web material constituting a component of at least part of the front and/or back panels of the article, the method comprising:

feeding a pair of continuous lengths of said substantially non-elastic web material intended to form the waistband substantially in parallel in said feeding direction and spaced apart a distance, said substantially non-elastic web materials each having two longitudinal side edges;

feeding a pair of continuous lengths of said elastic web material intended to form at least part of the front panel and the back panel, respectively, substantially in parallel and spaced apart a distance in said feeding direction, said elastic web materials each having two longitudinal side edges;

bringing each of said substantially non-elastic web materials to overlap a distance at their longitudinal edges facing each other, with a respective one of the lengths of the elastic web material and joining said overlapping side edges with each other; and providing at least one elongate elastic member to each of the continuous lengths of substantially non-elastic web material and joining the elongate elastic members to said respective non-elastic web material;

feeding a continuous length of a substantially non-elastic web material intended to form a crotch portion web material in said feeding direction between said pair of elastic web materials, said crotch portion web material having a pair of longitudinal side edges and is at its longitudinal side edges joined in an overlapping manner to the respective longitudinal side edges of the elastic web materials;

wherein each of said elastic web materials is stretched to a length which exceeds its untensioned length with at least 10% while being joined to the substantially non-elastic crotch portion web material.

23. A pant-type absorbent article, said article comprising:
a core region having an absorbent core and a chassis, said chassis comprising a front panel, a back panel and an elastic waistband, each of the front and back panels having a waist edge and a pair of side edges,
the front and back panels being joined to each other along two opposite side edges to define a waist-opening and a pair of leg-openings,
at least one of the front and back panels comprising an elastic web material constituting the sole component of at least part of the one front or back panel,
the elastic waistband being joined to the waist edge of at least one of the front and back panels,
wherein the elastic waistband comprises a first ply and a second ply of substantially non-elastic web material enclosing between them at least one elongate elastic member,
said article having a longitudinal and a transverse direction, said first ply of substantially non-elastic web material being secured to one side of said elastic web material at the waist edge of at least one of the front and back panels and said second ply of substantially non-elastic web material being secured to the opposite side of said elastic web material just opposite said first ply, the first and second plies being secured to the elastic web material while the elastic web material is in a stretched condition having a length which exceeds at least 10% of its untensioned length, the first and second plies of substantially non-elastic web material with said elastic web material held there between forming a waistband seam, wherein the first and second plies of substantially non-elastic material form gathers along said waistband seam when said elastic web material is in a relaxed position.

24. The pant-type absorbent article as claimed in claim 17, wherein said elastic waistband is formed from a folded substantially non-elastic web material so as to form said first and second plies enclosing said at least one elongate elastic member.

25. The absorbent article as claimed in claim 17, wherein a crotch panel of a substantially inelastic web material is arranged in a crotch portion of the article, said crotch pane being joined to the front and back panels comprising said elastic web material.

26. The absorbent article as claimed in claim 1, wherein the first and second plies are secured to the elastic web material while the elastic web material is in a stretched condition having a length which exceeds at least 20% of its untensioned length.

27. The absorbent article as claimed in claim 1, wherein the first and second plies are secured to the elastic web material while the elastic web material is in a stretched condition having a length which exceeds at least 30% of its untensioned length.

28. The absorbent article as claimed in claim 23, wherein the first and second plies are secured to the elastic web material while the elastic web material is in a stretched condition having a length which exceeds at least 20% of its untensioned length.

29. The absorbent article as claimed in claim 23, wherein the first and second plies are secured to the elastic web material while the elastic web material is in a stretched condition having a length which exceeds at least 30% of its untensioned length.

30. The absorbent article as claimed in claim 1, wherein the at least one elongate elastic member is not present within said waistband seam.

31. The absorbent article as claimed in claim 23, wherein the at least one elongate elastic member is not present within said waistband seam.

* * * * *